United States Patent [19]

Mark

[11] Patent Number: 4,554,110
[45] Date of Patent: Nov. 19, 1985

[54] PROCESS FOR THE PREPARATION OF AROMATIC CARBONATES

[75] Inventor: Victor Mark, Evansville, Ind.

[73] Assignee: General Electric Company, Mt. Vernon, Ind.

[21] Appl. No.: 565,888

[22] Filed: Dec. 27, 1983

[51] Int. Cl.$^4$ .............................................. C07C 68/06
[52] U.S. Cl. ...................................... 260/463; 556/83
[58] Field of Search ......................................... 260/463

[56] References Cited

U.S. PATENT DOCUMENTS

| | | | |
|---|---|---|---|
| 3,376,329 | 4/1968 | Kobetz et al. | 260/429.7 |
| 3,466,311 | 9/1969 | Mizuno et al. | 260/429.7 |
| 3,493,592 | 2/1970 | Shapiro et al. | 260/429.7 |
| 3,853,960 | 12/1974 | Crowther | 260/482 B |

OTHER PUBLICATIONS

Thieme et al., *Chemical Abstracts:* vol. 81:106342a, (1974).
Mitsui Toatsu Chemicals, Inc., *Chemical Abstracts:* vol. 96:68355g, (1982).
Narula et al., *Indian Journal Chem.*, vol. 17A, 1/1979, pp. 98–100.
Cummins, *Aust. J. Chem.*, 1965, 18, pp. 98–101.
Yamakazi et al., *Chemical Abstracts:* vol. 91:92272v, (1979).

*Primary Examiner*—Donald G. Daus
*Assistant Examiner*—Stephen M. Kapner
*Attorney, Agent, or Firm*—Myron B. Kapustij; Martin B. Barancik

[57] ABSTRACT

An improved process for the preparation of aromatic carbonates selected from aliphatic aromatic carbonates, diaromatic carbonates, and mixtures thereof comprising reacting a phenolic compound with a dialiphatic carbonate or an aliphatic aromatic carbonate in the presence of a catalytic amount of at least one catalyst selected from polymeric tin compounds containing recurring structural units represented by the general formula

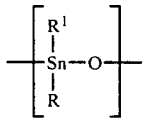

wherein:
R is selected from monovalent hydrocarbon radicals; and
$R^1$ is selected from monovalent hydrocarbon radicals.

12 Claims, No Drawings

PROCESS FOR THE PREPARATION OF AROMATIC CARBONATES

BACKGROUND OF THE INVENTION

Organic carbonates such as the dialiphatic carbonates, aliphatic aromatic carbonates, and diaromatic carbonates are generally conventionally prepared by the reaction of phenols or alcohols with phosgene in the presence of acid binding agents such as the organic bases or inorganic bases. However, due to the toxicity of phosgene it is sometimes desirable to avoid the use of phosgene in the preparation of these organic carbonates.

Since the dialiphatic carbonates, such as the dialkyl carbonates, may be prepared from alcohols by routes other than those utilizing phosgene, i.e., catalytically from carbon monoxide and oxygen, it is possible to prepare the aliphatic aromatic carbonates and the diaromatic carbonates from these dialiphatic carbonates and phenols without using phosgene. Such phosgene free processes are disclosed in U.S. Pat. Nos. 4,045,464 and 4,182,726. These patents disclose the preparation of alkyl aryl carbonates and diaryl carbonates by the reaction of phenols with dialkyl carbonates or alkyl aryl carbonates in the presence of a Lewis acid catalyst. The Lewis acid catalysts disclosed in these patents are compounds having the formulae $AlX_3$, $TiX_3$, $UX_4$, $TiX_4$, $VOX_3$, $VX_5$, $ZnX_2$, $FeX_3$, and $SnX_4$, wherein X is halogen, acetoxy, alkoxy, or aryloxy.

It would, however, be advantageous if a transesterification process could be provided which is more efficient, from the standpoint of providing higher conversion rates of the dialkyl carbonates to the alkyl aryl carbonates and the diaryl carbonates, particularly to the diaryl carbonates, than the presently available processes. It is, therefore, an object of the instant invention to provide such a process.

SUMMARY OF THE INVENTION

The instant invention is directed to a transesterification process for the preparation of aliphatic aromatic carbonates and diaromatic carbonates from dialiphatic carbonates utilizing a catalyst which exhibits improved catalytic activity as compared to presently utilized conventional Lewis acid catalysts. More particularly, the present invention is directed to a transesterification process for the preparation of aliphatic aromatic carbonates and diaromatic carbonates utilizing a catalytic amount of a catalyst which is selected from the polymers of oxy(dihydrocarbon substituted stannylene).

DESCRIPTION OF THE INVENTION

It has now been found that the conversion of dialkyl carbonates to alkyl aryl carbonates and diaryl carbonates via a transesterification process can be efficiently and facily accomplished by utilizing a catalytic amount of a polymeric oxy(dihydrocarbon substituted stannylene) catalyst.

The polymeric oxy(dihydrocarbon substituted stannylene) catalysts of the instant invention contain repeating structural units represented by the general formula

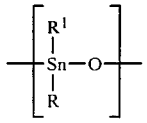

wherein:
R is selected from monovalent hydrocarbon radicals; and
$R^1$ is selected from monovalent hydrocarbon radicals.

The monovalent hydrocarbon radicals represented by R and $R^1$ are selected from the monovalent aliphatic hydrocarbon radicals and the monovalent aromatic hydrocarbon radicals. The monovalent aliphatic hydrocarbon radicals inlcude the alkyl radicals and the cycloalkyl radicals. The preferred alkyl radicals represented by R and $R^1$ are those containing from 1 to about 18 carbon atoms. These include the straight chain and the branched alkyl radicals. Some illustrative examples of these alkyl radicals include methyl, ethyl, propyl, isopropyl, butyl, tertiarybutyl, pentyl, neopentyl, hexyl, heptyl and undecyl. The preferred cycloalkyl radicals are those containing from 4 to about 7 ring carbon atoms. Some illustrative nonlimiting examples of these cycloalkyl radicals include cyclobutyl, cyclopentyl, methylcyclohexyl, cyclohexyl, and cycloheptyl.

The monovalent aromatic hydrocarbon radicals represented by R and $R^1$ include the aryl, aralkyl, and alkaryl radicals. The preferred aryl radicals are those containing from 6 to 12 carbon atoms and include phenyl, biphenyl and naphthyl. The preferred aralkyl and alkaryl radicals represented by R and $R^1$ are those containing from 7 to about 18 carbon atoms.

Some illustrative non-limiting examples of the catalysts containing the recurring structural units of Formula I include poly[oxy(dibutyl stannylene)], poly[oxy(dioctyl stannylene)], poly[oxy(butyl phenyl stannylene)], poly[oxy(methyl propyl stannylene)], poly[oxy(diphenyl stannylene)], and poly[oxy(dipropyl stannylene)].

The polymeric oxy(dihydrocarbon substituted stannylene) compounds of the instant invention may contain from about 3 to about 100 repeating structural units of Formula I in the polymer chain.

More particularly, the polymeric [oxy(dihydrocarbon substituted stannylene)] compounds useful as catalysts in the process of the instant invention may be represented by the general formula

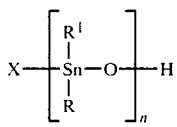

wherein:
R and $R^1$ are as defined hereinafore;
X is selected from the OH radical and halogen radicals, preferably the chlorine radical; and
n is a positive integer having a value of from 3 to about 100, and preferably from about 5 to about 50.

The aromatic carbonates which may be prepared by the process of the instant invention utilizing a catalytic amount of at least one catalyst of the instant invention include the aliphatic aromatic carbonates and the diaromatic carbonates. The aliphatic aromatic carbonates may be represented by the general formula $$\text{Ar}-\text{O}-\overset{\overset{\text{O}}{\|}}{\text{C}}-\text{O}-\text{R}^2 \qquad \text{III.}$$

wherein:
$R^2$ is selected from monovalent aliphatic hydrocarbon radicals; and
Ar is selected from monovalent aromatic radicals.

The preferred monovalent aliphatic hydrocarbon radicals represented by $R^2$ are the alkyl radicals and the cycloalkyl radicals. The preferred alkyl radicals are those containing from 1 to about 12 carbon atoms. These alkyl radicals include the straight chain alkyl radicals and the branched alkyl radicals. Some illustrative non-limiting examples of these alkyl radicals include methyl, ethyl, propyl, isopropyl, butyl, tertiarybutyl, pentyl, neopentyl, hexyl, and heptyl. The preferred cycloalkyl radicals represented by $R^2$ are those containing from 4 to about 7 ring carbon atoms. These include, but are not limited to, cyclobutyl, cyclopentyl, methylcyclohexyl, cyclohexyl, and cycloheptyl. The more preferred monovalent aliphatic radicals represented by $R^2$ are the lower alkyl radicals containing from 1 to about 4 carbon atoms.

The monovalent aromatic radicals represented by Ar include the aryl radicals containing from 6 to 12 carbon atoms. These include phenyl, naphthyl, and biphenyl. Preferred aryl radicals represented by Ar are those having the general formula

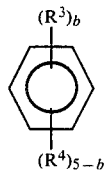

wherein:
$R^3$ is independently selected from monovalent hydrocarbon radicals and halogen radicals;
$R^4$ is hydrogen; and
b is a positive integer having a value of from 0 to 5 inclusive.

The monovalent hydrocarbon radicals represented by $R^3$ include the alkyl radicals, cycloalkyl radicals, aryl radicals, alkaryl radicals, and aralkyl radicals.

The preferred alkyl radicals represented by $R^3$ are those containing from 1 to about 10 carbon atoms. These alkyl radicals include the straight chain alkyl radicals and the branched alkyl radicals. The preferred cycloalkyl radicals are those containing from 4 to about 7 ring carbon atoms. The preferred aryl radicals represented by $R^3$ are those containing from 6 to 12 ring carbon atoms and include phenyl, naphthyl, and biphenyl. The preferred aralkyl and alkaryl radicals represented by $R^3$ are those containing from 7 to about 14 carbon atoms.

The preferred halogen radicals represented by $R^3$ are chlorine and bromine.

The diaromatic carbonates may be represented by the general formula $$\text{Ar}-\text{O}-\overset{\overset{\text{O}}{\|}}{\text{C}}-\text{O}-\text{Ar} \qquad \text{V.}$$

wherein Ar is as defined hereinafore.
In Formula V both of the Ar radicals may be the same, or they may be different.

The aliphatic aromatic carbonates of the instant invention may be prepared by the reaction of a phenol of the general formula Ar—OH wherein Ar is as defined hereinafore, with a dialiphatic carbonate of the general formula $$\text{R}^2-\text{O}-\overset{\overset{\text{O}}{\|}}{\text{C}}-\text{O}-\text{R}^2 \qquad \text{VI.}$$

wherein $R^2$ is as defined hereinafore, in the presence of a catalytic amount of at least one catalyst of the instant invention.

The reaction of the phenol with the dialiphatic carbonate may be represented by the formula (a) $\text{R}^2-\text{O}-\overset{\overset{\text{O}}{\|}}{\text{C}}-\text{O}-\text{R}^2 +$ $\text{Ar}-\text{OH} \underset{\phantom{\text{cat.}}}{\overset{\text{cat.}}{\rightleftharpoons}} \text{R}^2-\text{O}-\overset{\overset{\text{O}}{\|}}{\text{C}}-\text{O}-\text{Ar} + \text{R}^2-\text{OH}$ wherein $R^2$ and Ar are as defined hereinafore, and cat. is a catalytic amount of the catalyst of the instant invention.

The diaromatic carbonates of the instant invention may be prepared by either one of two methods. The first method involves reacting the aliphatic aromatic carbonate of Formula III with a phenol, in the presence of a catalytic amount of the catalyst of the instant invention. This reaction may be represented by the general formula (b) $\text{R}^2-\text{O}-\overset{\overset{\text{O}}{\|}}{\text{C}}-\text{O}-\text{Ar} +$ $\text{Ar}-\text{OH} \underset{\phantom{\text{cat.}}}{\overset{\text{cat.}}{\rightleftharpoons}} \text{Ar}-\text{O}-\overset{\overset{\text{O}}{\|}}{\text{C}}-\text{O}-\text{Ar} + \text{R}^2-\text{OH}$ wherein $R^2$, Ar and cat. are as defined hereinafore.

The second method involves the reaction of the aliphatic aromatic carbonate with itself or with another aliphatic aromatic carbonate in the presence of a catalytic amount of the catalyst of the instant invention. This reaction may be represented by the general formula (c) $2\ \text{R}^2-\text{O}-\overset{\overset{\text{O}}{\|}}{\text{C}}-\text{O}-\text{Ar} \underset{\phantom{\text{cat.}}}{\overset{\text{cat.}}{\rightleftharpoons}} \text{Ar}-\text{O}-\overset{\overset{\text{O}}{\|}}{\text{C}}-\text{O}-\text{Ar} +$ $\text{R}^2-\text{O}-\overset{\overset{\text{O}}{\|}}{\text{C}}-\text{O}-\text{R}^2$ wherein Ar, $R^2$, and cat. are as defined hereinafore.

The reactions depicted by Formulae (a), (b), and (c) may be carried out in the liquid phase, with or without the presence of a solvent, at temperatures of from about 60° C. to about 300° C., preferably from about 150° C. to about 250° C. These reactions may be carried out at pressures ranging from subatmospheric pressures to superatmospheric pressures, e.g., from about 0.1 to about 50 atmospheres. These reactions proceed readily, in the presence of the catalyst of the instant invention, at atmospheric pressure.

Since the reactions depicted by Formulae (a) and (b) are equilibrium reactions, it is advantageous to remove the alcohol formed so as to continuously shift the equilibrium until the reactions reach completion. Since the alcohol is most conveniently removed by distillation it is desirable that the reactants in the equations depicted by Formulae (a) and (b) are so selected that the $R^2$—OH byproduct has a lower boiling point than the Ar—OH reactant and thus can be distilled off as it is formed. It is for this reason that the lower dialiphatic carbonates or the lower aliphatic aromatic carbonates are the preferred reactants in the processes of the instant invention, i.e., $R^2$ is a lower alkyl radical containing from 1 to about 4 carbon atoms in the dialiphatic carbonates and the aliphatic aromatic carbonates.

The preparation of the diaromatic carbonates by the reaction depicted by Formula (c) may also be conveniently achieved by the distillation of the dialiphatic carbonate coproduct. For this reason, it is also preferred that the aliphatic aromatic carbonate reactant be a lower aliphatic aromatic carbonate so that the dialiphatic carbonate coproduct may be readily distilled off, i.e., $R^2$ in the aliphatic aromatic carbonate is a lower alkyl radical containing from 1 to about 4 carbon atoms.

In the preparation of the diaromatic carbonates of the instant invention it is preferred that the reaction process be continuous and be carried out in the same reaction vessel. That is to say, once the reaction of the dialiphatic carbonate with the phenol to form the aliphatic aromatic carbonate has ocurred, the aliphatic aromatic carbonate product is not removed but is allowed to further react with the remaining phenol reactant to form the diaromatic carbonate.

While theoretically it requires two moles of phenol for every mole of dialiphatic carbonate to produce the diaromatic carbonate, in practice it is generally preferred to use an excess of the phenol reactant. Thus, for example, it is generally preferred to use an excess of phenol when reacting the dialiphatic carbonate with the phenol to form the aliphatic aromatic carbonate, and it is also generally preferred to utilize an excess of phenol reactant when reacting the phenol with the aliphatic aromatic carbonate to form the diaromatic carbonate. Since it is generally preferred to employ a continuous process for the preparation of the diaromatic carbonates, it is generally preferred to use more than two moles of the phenol reactant for every mole of dialiphatic carbonate reactant present.

The amount of the catalyst of the instant invention utilized in the exchange reactions described herein is a catalytic amount. By catalytic amount is meant an amount effective to catalyze the transesterification reaction for the preparation of the aliphatic aromatic carbonates from the dialiphatic carbonates and phenols or the diaromatic carbonates from the aliphatic aromatic carbonates and phenols. Generally this amount is in the range of from about 0.01 to about 20 weight percent, based on the amounts of the dialiphatic carbonates or aliphatic aromatic carbonates utilized as the reactants, and preferably from about 0.1 to about 15 weight percent.

It is further contemplated that the instant catalysts would be effective in catalyzing any transesterification reaction. Among these transesterification reactions is the formation of polycarbonates via a transesterification reaction. Thus, while the instant disclosure and examples are directed to the formation of aliphatic aromatic carbonates and diaromatic carbonates from dialiphatic carbonates and aliphatic aromatic carbonates, respectively, it is contemplated that the catalysts of the instant invention would be effective in the formation of other esters, particularly aromatic esters, via a transesterification process.

DESCRIPTION OF THE PREFERRED EMBODIMENT

In order to more fully and clearly illustrate the present invention the following examples are set forth. It is intended that the examples be considered as illustrative rather than limiting the invention as disclosed and claimed herein. In the examples all parts and percentages are on a weight basis, unless otherwise indicated.

The following examples illustrate the preparation of aliphatic aromatic (alkyl aryl) carbonates and diaromatic (diaryl) carbonates utilizing Lewis acid catalysts falling outside the scope of the instant invention. These examples are presented for comparative purposes only.

EXAMPLE 1

To a 500 milliliter 4-necked flask equipped with a mechanical stirrer, thermometer, and a one-foot long column, filled with glass helices and capped by a distillation head with a thermometer and reflux condenser, are charged 188.2 grams (2.0 mole) of phenol and 4 grams of dibutyltin maleate catalyst. This mixture is heated, with stirring, to 180° C. When this temperature is reached 29.5 grams (0.25 mole) of diethyl carbonate are added dropwise from the addition funnel during a one hour period. After addition of the diethyl carbonate is complete the ethyl alcohol liberated is continuously removed from the reaction mixture by distillation. The reaction is continued for a period of 24 hours. At the end of the 24 hour reaction period the reaction mixture is stripped under water aspirator vacuum to distill over the remaining unreacted phenol. The remaining reaction mixture is weighed and analyzed by gas chromatography for the ethyl phenyl carbonate and the diphenyl carbonate. The results are set forth in Table I.

EXAMPLE 2

The procedure of Example 1 is substantially repeated except that the 4 grams of dibutyltin maleate catalyst are replaced with 4 grams of dibutyltin dibutoxide catalyst. The results are set forth in Table I.

EXAMPLE 3

The procedure of Example 1 is substantially repeated except that the 4 grams of dibutyltin maleate catalyst are replaced with 4 grams of triphenyltin hydroxide catalyst. The results are set forth in Table I.

The following examples illustrate the preparation of aliphatic aromatic (alkyl aryl) carbonates and diaromatic (diaryl) carbonates from dialiphatic (dialkyl) carbonates utilizing the catalysts of the instant invention.

EXAMPLE 4

To a 500 milliliter 4-necked flask equipped with a mechanical stirrer, thermometer, and a one-foot long column, filled with glass helices and capped by a distillation head with a thermometer and reflux condenser, are charged 188.2 grams (2.0 moles) of phenol and 4 grams of poly[oxy(dibutylstannylene)] catalyst. This mixture is heated, with stirring, to 180° C. When this temperature is reached 29.5 grams (0.25 mole) of diethyl carbonate are added dropwise from the addition funnel during a one hour period. After addition of the diethyl carbonate is complete the ethyl alcohol liberated is continuously removed from the reaction mixture by distillation. The reaction is continued for 5 hours. At the end of the 5 hour reaction period the reaction mixture is stripped under water aspirator vacuum to distill over the remaining unreacted phenol reactant. The remaining reaction mixture is weighed and analyzed by gas chromatography for the ethyl phenyl carbonate and the diphenyl carbonate. The results are set forth in Table I.

EXAMPLE 5

The procedure of Example 4 is substantially repeated except that the reaction is carried out for a period of 7 hours. Table I illustrates the results.

EXAMPLE 6

The procedure of Example 4 is substantially repeated except that the reaction is carried out for a period of 23 hours. The results are set forth in Table I.

EXAMPLE 7

The procedure of Example 4 is substantially repeated except that the 4 grams of poly[oxy(dibutylstannylene)] catalyst are replaced with 4 grams of poly[oxy(dioctylstannylene)] catalyst and the reaction is carried out for a period of 24 hours. The results are set forth in Table I.

EXAMPLE 8

The procedure of Example 4 is substantially repeated except that the 4 grams of poly[oxy(dibutylstannylene)] catalyst are replaced with 4 grams of poly[oxy(butyl phenyl stannylene)] catalyst and the reaction is carried out for a period of 24 hours. The results are set forth in Table I.

EXAMPLE 9

The procedure of Example 4 is substantially repeated except that the 29.5 grams (2.0 moles) of diethyl carbonate are replaced with 22.5 grams (0.25 mole) of dimethyl carbonate and the reaction is carried out for a period of 24 hours. The results are set forth in Table I.

EXAMPLE 10

The procedure of Example 9 is substantially repeated except that the 4 grams of the poly[oxy(dibutylstannylene)] catalyst are replaced with 1 gram of poly[oxy(dibutystannylene)] catalyst. The results are set forth in Table I.

TABLE I

| Example No. | Catalyst Amount (gms.) | Reaction Time (hrs.) | Alkyl Aryl Carbonate (mole %) | Diaryl Carbonate (mole %) | Diaryl Carbonate Yield (mole % of theoretical) |
|---|---|---|---|---|---|
| 1 | 4.0 | 24 | 7.8 | 8.0 | 19.0 |
| 2 | 4.0 | 24 | 5.2 | 1.0 | 2.4 |
| 3 | 4.0 | 24 | 6.0 | 0 | 0 |
| 4 | 4.0 | 5 | 10.3 | 4.4 | 10.5 |
| 5 | 4.0 | 7 | 9.8 | 6.8 | 16.3 |
| 6 | 4.0 | 23 | 5.0 | 26.1 | 62.4 |
| 7 | 4.0 | 24 | 1.1 | 32.2 | 77.0 |
| 8 | 4.0 | 24 | 10.2 | 10.8 | 25.8 |
| 9 | 4.0 | 24 | 0 | 16.0 | 67.8 |
| 10 | 1.0 | 24 | 0 | 15.7 | 67.2 |

EXAMPLE 11

The procedure of Example 4 is substantially repeated except that the 188.2 grams (2.0 moles) of phenol are replaced with 244.2 grams (2.0 moles) of 2,6-xylenol and the reaction is carried out for a period of 24 hours. At the end of the 24 hour reaction period the diethyl carbonate is converted to ethyl 2,6-xylyl carbonate as evidenced by gas chromatographic analysis which shows its emergence peak at 7.03 minutes. Under comparable conditions the emergence peak of ethyl phenyl carbonate is at 5.54 minutes.

EXAMPLE 12

The procedure of Example 7 is substantially repeated except that the 188.2 grams (2.0 moles) of phenol are replaced with 200 grams (2.0 moles) of o-chlorophenol. Ethyl 2-chlorophenyl carbonate and bis(2-chlorophenyl) carbonate are identified as the products by gas chromatographic analysis with the gas chromatographic elution time for ethyl 2-chlorophenyl carbonate occurring at 7.35 minutes and the gas chromatographic elution time for bis(2-chlorophenyl)carbonate occurring at 15.64 minutes.

As illustrated by the data in Table I the catalysts of the instant invention are more efficent than the conventional Lewis acid catalysts (Examples 1–3) in the transesterification processes of the instant invention. A comparison of Examples 6–10 with Examples 1–3 shows that for comparable reaction times significantly larger amounts of the diphenyl carbonates are formed by the utilization of the polymeric catalysts of the instant invention than by using the conventional Lewis acid catalysts falling outside the scope of the instant invention.

Obviously, other modifications and variations of the present invention are possible in light of the above teachings. It is, therefore, to be understood that changes may be made in the particular embodiments of the invention described which are within the full intended scope of the invention as defined by the appended claims.

What is claimed is:

1. An improved process for the preparation of an aromatic carbonate selected from aliphatic aromatic carbonates represented by the formula

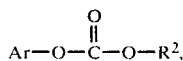

diaromatic carbonates represented by the formula

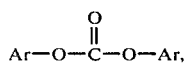

and mixtures thereof which comprises reacting a phenolic compound with a dialiphatic carbonate represented by the formula

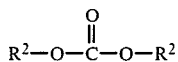

or an aliphatic aromatic carbonate represented by the formula

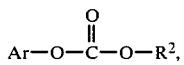

wherein $R^2$ is independently selected from monovalent aliphatic radicals having from 1 to about 12 carbon atoms and Ar is independently selected from aromatic radicals having from 6 to 12 ring carbon atoms, in the presence of a catalytic amount of a catalyst, the improvement comprising utilizing as the catalyst a polymeric tin compound containing recurring structural units represented by the formula

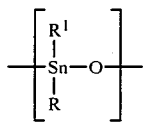

wherein:
R is selected from monovalent hydrocarbon radicals having from 1 to about 18 carbon atoms; and
$R^1$ is selected from monovalent hydrocarbon radicals having from 1 to about 18 carbon atoms.

2. The process of claim 1 wherein said monovalent hydrocarbon radicals R and $R^1$ are selected from monovalent aliphatic hydrocarbon radicals having from 1 to about 18 carbon atoms and monovalent aromatic hydrocarbon radicals having from 6 to 12 ring carbon atoms.

3. The process of claim 2 wherein said monovalent aliphatic hydrocarbon radicals are selected from alkyl radicals having from 1 to about 18 carbon atoms and cycloalkyl radicals having from 4 to about 7 ring carbon atoms.

4. The process of claim 2 wherein said monovalent aromatic hydrocarbon radicals are selected from aryl radicals having from 6 to 12 ring carbon atoms, aralkyl radicals having from 7 to about 18 carbon atoms, and alkaryl radicals having from 7 to about 18 carbon atoms.

5. The process of claim 2 wherein R and $R^1$ are selected from alkyl radicals.

6. The process of claim 2 wherein $R^1$ is selected from alkyl radicals and R is selected from aryl radicals.

7. The process of claim 6 wherein said aryl radical is phenyl.

8. The process of claim 2 wherein said catalytic amount is in the range of from about 0.01 to about 20 weight percent, based on the amounts of aliphatic aromatic carbonate reactant or dialiphatic carbonate reactant utilized.

9. The process of claim 8 wherein said amount is in the range of from about 0.1 to about 15 weight percent.

10. The process of claim 9 wherein said catalyst is poly[oxy(dibutyl stannylene)].

11. The process of claim 9 wherein said catalyst is poly[oxy(dioctylstannylene)].

12. The process of claim 9 wherein said catalyst is poly[oxy(butyl phenyl stannylene)].

* * * * *